United States Patent
Wei et al.

(10) Patent No.: US 8,791,045 B2
(45) Date of Patent: Jul. 29, 2014

(54) NON-TACKY WETNESS INDICATOR COMPOSITION FOR APPLICATION ON A POLYMERIC SUBSTRATE

(75) Inventors: Ning Wei, Roswell, GA (US); Xuedong Song, Alpharetta, GA (US); JinHo Ryu, Yongin-si (KR); JunMo Gil, DaeJeon (KR)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 448 days.

(21) Appl. No.: 13/292,612

(22) Filed: Nov. 9, 2011

(65) Prior Publication Data

US 2013/0116644 A1    May 9, 2013

(51) Int. Cl.
| | |
|---|---|
| *B41M 5/128* | (2006.01) |
| *A61L 15/56* | (2006.01) |
| *A61F 13/42* | (2006.01) |
| *C09D 11/02* | (2014.01) |
| *G01N 21/81* | (2006.01) |
| *G01N 31/22* | (2006.01) |

(52) U.S. Cl.
CPC .............. *B41M 5/128* (2013.01); *A61F 13/42* (2013.01); *A61L 15/56* (2013.01); *C09D 11/02* (2013.01); *G01N 21/81* (2013.01); *G01N 31/222* (2013.01)
USPC ..................... 503/205; 106/31.16; 106/31.18; 106/31.22

(58) Field of Classification Search
CPC ........ B41M 5/128; A61L 15/56; A61F 13/42; C09D 11/02; G01N 21/81; G01N 31/222
USPC ..................... 503/200–226; 106/31.16–31.22; 604/361
See application file for complete search history.

(56) References Cited

U.S. PATENT DOCUMENTS

| | | |
|---|---|---|
| 4,020,156 A | 4/1977 | Murray et al. |
| 4,880,921 A | 11/1989 | Bodor |
| 5,130,290 A | 7/1992 | Tanimoto |
| 5,133,958 A | 7/1992 | Stuckler |
| 5,197,958 A | 3/1993 | Howell |
| 5,389,093 A | 2/1995 | Howell |
| 5,622,944 A | 4/1997 | Hale et al. |
| 5,827,913 A | 10/1998 | Baetzold et al. |
| 5,958,870 A | 9/1999 | Declercq et al. |
| 6,369,290 B1 | 4/2002 | Glaug et al. |

(Continued)

FOREIGN PATENT DOCUMENTS

| | | |
|---|---|---|
| EP | 0752465 A1 | 1/1997 |
| EP | 0771785 B1 | 1/2002 |

(Continued)

OTHER PUBLICATIONS

Co-pending U.S. Appl. No. 13/230,102, filed Sep. 12, 2011, by Song et al. for "Wetness Indicator Having Varied Hues."

*Primary Examiner* — Bruce H Hess
(74) *Attorney, Agent, or Firm* — Denise L. Stoker (57) ABSTRACT

The invention describes a color-developing composition that contains at least three major components: (1) a leuco dye or a combination of leuco dyes, (2) an color-developer or a combination of color-developers that can form colored complexes with the leuco dyes, and (3) a desensitizer to temporarily remove the effect of the developer so the leuco dye appears in its colorless form. An optional binder may be included so that the composition may be applied to a substrate as an ink. The ink composition may be applied to synthetic polymeric substrates and other substrates that are incorporated into absorbent articles or personal care products.

20 Claims, 3 Drawing Sheets

(56) References Cited

U.S. PATENT DOCUMENTS

| | | |
|---|---|---|
| 6,458,456 B1 | 10/2002 | Zainiev et al. |
| 6,586,639 B2 | 7/2003 | Murayama et al. |
| 6,677,297 B2 | 1/2004 | Frerot |
| 7,056,878 B2 | 6/2006 | Fender et al. |
| 7,105,715 B2 | 9/2006 | Carlucci et al. |
| 7,229,958 B2 | 6/2007 | Koehle et al. |
| 7,407,670 B2 | 8/2008 | Six et al. |
| 7,501,536 B2 | 3/2009 | Jaunky et al. |
| 7,550,416 B2 | 6/2009 | Woo et al. |
| 7,655,830 B2 | 2/2010 | Flohr et al. |
| 7,758,888 B2 | 7/2010 | Lapidot et al. |
| 8,022,030 B2 | 9/2011 | Berthier et al. |
| 2003/0083513 A1 | 5/2003 | Murayama et al. |
| 2005/0131363 A1 | 6/2005 | Kim et al. |
| 2007/0021319 A1 | 1/2007 | Kohle et al. |
| 2007/0031485 A1 | 2/2007 | Ljusberg-wahren et al. |
| 2007/0081953 A1 | 4/2007 | Dahms |
| 2007/0105793 A1 | 5/2007 | Hendrix |
| 2007/0160553 A1 | 7/2007 | Kripp et al. |
| 2007/0270773 A1 | 11/2007 | Mackey |
| 2008/0139378 A1 | 6/2008 | Hildebrand et al. |
| 2008/0279253 A1 | 11/2008 | Macdonald et al. |
| 2008/0286224 A1 | 11/2008 | Vega et al. |
| 2009/0054860 A1 | 2/2009 | Young et al. |
| 2009/0156634 A1 | 6/2009 | Molino et al. |
| 2009/0221980 A1 | 9/2009 | Mosbacher et al. |
| 2009/0275908 A1 | 11/2009 | Song |
| 2010/0012017 A1 | 1/2010 | Miller |
| 2010/0030173 A1 | 2/2010 | Song et al. |
| 2010/0160299 A1 | 6/2010 | Baker, Jr. et al. |
| 2010/0221330 A1 | 9/2010 | Messadek |
| 2010/0227896 A1 | 9/2010 | Biedermann et al. |
| 2010/0248959 A1 | 9/2010 | Kato et al. |
| 2010/0307422 A1 | 12/2010 | Huck et al. |
| 2011/0015599 A1 | 1/2011 | Song et al. |
| 2011/0046571 A1 | 2/2011 | Waldhorn |
| 2011/0104023 A1 | 5/2011 | Nakatsubo et al. |
| 2011/0144603 A1 | 6/2011 | Song |
| 2011/0152805 A1 | 6/2011 | Gil |
| 2011/0250286 A1 | 10/2011 | Marcello et al. |
| 2012/0064136 A1 | 3/2012 | Baker, Jr. et al. |
| 2012/0121669 A1 | 5/2012 | Fontana et al. |
| 2012/0259098 A1 | 10/2012 | Baker, Jr. et al. |

FOREIGN PATENT DOCUMENTS

| | | |
|---|---|---|
| JP | 01-275511 A | 11/1989 |
| JP | 03-221039 A | 9/1991 |
| WO | WO 98/26808 A2 | 6/1998 |
| WO | WO 01/27234 A1 | 4/2001 |
| WO | WO 03/047558 A2 | 6/2003 |
| WO | WO 2008/068059 A2 | 6/2008 |
| WO | WO 2009/018368 A1 | 2/2009 |

NON-TACKY WETNESS INDICATOR COMPOSITION FOR APPLICATION ON A POLYMERIC SUBSTRATE

The present disclosure pertains to an indicator composition that changes color in the presence of an aqueous solution. In particular, the present disclosure pertains to a medium or ink that exhibits low tack when applied to various polymeric substrates and that when in the presence of an aqueous solution, changes from a largely colorless or pale appearance to a higher intensity color.

BACKGROUND

Many products, including consumer, health care, and professional products, are more effectively used by an end user when the product includes a feature that can communicate or signal to the user a particular condition or indicate the relative level or degree of use. One example is a visual indicator that causes the product to display a color. Color indicators can either indicate a change in a condition or a degree of use through a change from colorless to a color, or through an increase in color intensity.

Exemplary conditions that can be monitored with a color indicator include the presence of moisture. Exemplary consumer products that can be more effective and deliver more benefits to end users by incorporating a suitable color indicator include absorbent articles having synthetic polymeric substrates incorporated therein, such a diapers, training pants, incontinence products and the like. Such substrates are often used as liquid barriers.

Color indicators are well known and are available in various forms. Many known color indicators can be applied to substrates in liquid form at room temperature by various printing methods such as stamping, ink jet, flexographic and gravure printing methods. However, the presently available color-developing types of color indicators remain tacky after they are applied to synthetic polymeric substrates. Such color indicators are therefore not suitable for use in absorbent articles because at the very least, the tackiness causes manufacturing problems.

While the color-changing compositions known in the art provide certain benefits, there remains a need for a color-developing type of color indicator that can be applied to certain polymeric substrates and that exhibit low tack. There also remains a need for a composition that is durable, is non-leachable and that shows a readily-discernible color change when the composition is used in a product. Further, there remains a need for a composition having the above characteristics that can be applied to substrates using a printing technique.

SUMMARY OF THE INVENTION

The present disclosure relates in part to a color-developing composition for use in an indicator medium or ink solution. The color-developing composition includes a color-appearing leuco dye, a color-developer and a desensitizer. The desensitizer is a zwitterionic small molecule having a molecular weight of 100 to 800.

In another aspect of the disclosure, a color changing material is made from a substrate having an ink deposited thereon. The ink includes a color-appearing leuco dye, a color-developer and a desensitizer. The desensitizer is betaine and/or Girard's reagent.

In yet another aspect of the disclosure there is an absorbent article with a color-changing feature, the absorbent article having a topsheet, a backsheet having a garment-facing surface and an opposite body-facing surface and an absorbent core disposed between the topsheet and the back sheet. A color-changing composition including a leuco-dye and a developer is deposited onto the body-facing surface of the backsheet. The color-changing composition further includes a zwitterionic small molecule desensitizer having a molecular weight between 100 and 500.

Additional features and advantages of the present composition will be described in the following detailed description. It is understood that the foregoing general description and the following detailed description and examples are merely representative of the invention, and are intended to provide an overview for understanding the invention as claimed.

DETAILED DESCRIPTION

The present disclosure relates a color-developing composition that can be applied to a substrate surface by conventional printing techniques. The color-developing composition changes from a largely colorless or pale appearance to a visually distinct or vibrant color when the composition is exposed to a change in its immediate physical or chemical environment as a result of the introduction of an aqueous solution.

The present disclosure involves a color-developing composition that contains at least three major components: (1) a leuco dye or a combination of leuco dyes, (2) an electron-withdrawing color-developer agent or a combination of color-developers that can form colored complexes with the leuco dyes, and (3) a desensitizer or combinations of desensitizers to temporarily remove the effect of the developer so that the leuco dye appears in its largely colorless form until wetted with an aqueous solution. All of the foregoing components are dissolved together in a volatile organic-solvent medium to form a homogeneous solution.

In addition to the three main components, the homogeneous solution may contain a binder so that the solution may be used as an ink suitable for printing and that can be air-dried without heating. According to the disclosure, suitable binders include, but are not limited to compositions that consist of mainly organic soluble polymeric resins such as modified celluloses, polyesters and polyamides. Organic solvent-based varnishes are also suitable binding compositions.

Other additives may be used such as to adjust the physical properties of the composition. The composition may contain reagents to adjust the viscosity of the solution, or may include chemicals to improve adhesion of the composition to certain substrate surfaces upon drying. The composition may further include chemistry that tailors the composition's subsequent wettability on the substrate surface.

Leuco dyes are generally referred to as colorless or pale-colored basic dyes, because the dye molecules can acquire two forms, one of which is colorless. Although not intended to be bound by theory, it is believed that the color-developer agent functions as a Lewis acid, which withdraws electrons from the leuco dye molecule to generate a conjugated system. Hence, the leuco dye appears to manifest color from an originally colorless state.

For example, the spiro form of an oxazine is a colorless leuco dye; the conjugated system of the oxazine and another aromatic part of the molecule is separated by an sp3-hybridized "spiro" carbon. After protonating a part of the molecule, irradiation with UV-light or introducing other kind of such change, the bond between the spiro carbon and the oxazine interrupts, the ring opens, the spiro carbon achieves sp2 hybridization and becomes planar, the aromatic group rotates, aligns its π-orbitals with the rest of the molecule, and a conjugated system forms, with the ability to absorb photons of visible light, and therefore appear colorful.

The leuco dyes that may be employed can be selected from a variety of dyes including, for example, phthalide leuco dyes, triarylmethane leuco dyes, and fluoran leuco dyes. Examples may include (1) Triarylmethane-based dyes, e.g. 3,3-bis(p-dimethylaminophenyl)-6-dimethylaminophthalide, 3,3-bis (p-dimethylaminophenyl)phthalide, 3-(p-dimethylaminophenyl)-3-(1,2-dimethylindol-3-yl)phthalide, 3-(p-dimethylaminophenyl)-3-(2-methylindol-3-yl)phthalide, 3,3-bis(1,2-dimethylindol-3-yl)-5-dimethylaminophthalide, 3,3-bis(1,2-dimethylindol-3-yl)-6-dimethylaminophthalide, 3,3-bis(9-ethylcarbazol-3-yl)-6-dimethylaminophthalide, 3,3-bis(2-phenylindol-3-yl)-6-dimethylaminophthalide, 3-p-dimethylaminophenyl-3-(1-methylpyrrol-3-yl)-6-dimethylaminophthalide, etc. (2) Diphenylmethane-based dyes, e.g., 4,4'-bisdimethylaminobenzhydryl benzyl ether, N-halophenylleucoauramine, N-2,4,5-trichlorophenyl-leucoauramine, etc. (3) Lactam-based dyes, e.g., rhodamine-B-anilinolactam, rhodamine-(p-nitroanilino)lactam, rhodamine-(o-chloroanilino)lactam, etc. (4) Fluoran-based dyes, e.g., 3-dimethylamino-7-methoxyfluoran, 3-diethylamino-6-methoxyfluoran, 3-di-ethylamino-7-methoxyfluoran, 3-diethylamino-7-chlorofluoran, 3-diethylamino-6-methyl-7-chlorofluoran, 3-di-ethylamino-6,7-dimethylfluoran, 3-(N-ethyl-p-toluidino)-7-methylfluoran, 3-diethylamino-7-(N-acetyl-N-methylamino)fluoran, fluoran, 3-diethylamino-7-(N-methylamino)fluoran, 3-diethylamino-7-dibenzylaminofluoran, 3-diethylamino-7-(N-methyl-N-benzylamino)fluoran, 3-diethylamino-7-(N-chloroethyl-N-methylamino)fluoran, 3-diethylamino-7-N-diethylaminofluoran, 3-(N-ethyl-p-toluidino)-6-methyl-7-phenylaminofluoran, 3-(N-ethyl-p-toluidino)-6-methyl-7-(p-toluidino) fluoran, 3-diethylamino-6-methyl-7-phenylaminofluoran, 3-dibutylamino-6-methyl-7-phenylaminofluoran, 3-diethylamino-7-(2-carbomethoxyphenylamino)fluoran, 3-(N-cyclohexyl-N-methylamino)-6-methyl-7-phenylaminofluoran, 3-pyrrolidino-6-methyl-7-phenylaminofluoran, 3-piperidino-6-methyl-7-phenylaminofluoran, 3-diethylamino-6-methyl-7-(2,4-dimethylamino)fluoran, 3-diethylamino-7-(o-chlorophenylamino)fluoran, 3-dibutylamino-7-(o-chlorophenylamino)fluoran, 3-pyrrolidino-6-methyl-7-(p-butylphenylamino)fluoran, 3-(N-methyl-N-n-amylamino)-6-methyl-7-phenylaminofluoran, 3-(N-ethyl-N-n-amylamino)-6-methyl-7-phenylaminofluoran, 3-(N-ethyl-N-isoamylamino)-6-methyl-7-phenylaminofuluoran, 3-(N-methyl-N-n-hexylamino)-6-methyl-7-phenylaminofluoran, 3-(N-ethyl-N-n-hexylamino)-6-methyl-7-phenylaminofluoran, 3-(N-ethyl-N-β-ethylhexylamino)-6-methyl-7-phenylaminofluoran, etc. The basic dyes useful in this invention are not limited to those exemplified above, and at least two of them can be used in admixture.

Examples of suitable developers include bisphenol A, zinc chloride, zinc salicylate, and phenol resins. Other examples of color developing materials to be used conjointly with the leuco dyes may include: 4-tert-butylphenol, α-naphthol, β-naphthol, 4-acetylphenol, 4-tert-octylphenol, 4,4'-sec-butylidenephenol, 4-phenylphenol, 4,4'-dihydroxydiphenylmethane, 4,4'-isopropylidene diphenol, hydroquinone, 4,4'-cyclohexylidene diphenol, 4,4-dihydroxy diphenylsulfide, 4,4'-thiobis(6-tert-butyl-3-methylphenol), 4,4'-dihydroxydiphenyl sulfone, hydroquinone monobenzyl ether, 4-hydroxybenzophenone, 2,4-dihydroxybenzophenone, 2,4,4'-trihydroxybenzophenone, 2,2',4,4'-tetrahydroxybenzophenone, dimethyl 4-hydroxyphthalate, methyl 4-hydroxybenzoate, ethyl 4-hydroxybenzoate, propyl 4-hydroxybenzoate, sec-butyl 4-hydroxybenzoate, pentyl 4-hydroxybenzoate, phenyl 4-hydroxybenzoate, benzyl 4-hydroxybenzoate, tolyl 4-hydroxybenzoate, chlorophenyl 4-hydroxybenzoate, phenylpropyl 4-hydroxybenzoate, phenethyl 4-hydroxybenzoate, p-chlorobenzyl 4-hydroxybenzoate, p-methoxybenzyl 4-hydroxybenzoate, novolak type phenol resins, phenol polymers and like phenol compounds.

Desirably, the functional desensitizer of the present disclosure is of low molecular weight. Most desirably, the desensitizer is a zwitterionic molecule having a molecular weight of about 100 to about 500, and high solubility in water and organic solvents. One such desensitizer is betaine:

It may also be desirable to use a zwitterionic molecule having a molecular weight of about 100 to about 800; or in the alternative, about 200 to about 400. Suitable types of betaine include poly sugar betaine C, Betaine ester-menthol and Betaine hydrochloride. Other zwitterionic molecules include 2-(methacryloyloxy)ethyl 3-sulfopropyl)ammonium hydroxide.

All the components in the color-changing composition are soluble in one or more volatile organic solvents, such as solvents used for flexographic and gravure printing. Like the leuco dyes, the color-developers generally exhibit good solubility in organic solvents. Suitable volatile organic solvents may include, for example, ethanol, methanol, propanol, isopropanol, butanol, acetone, tetrahydrofuran (THF), benzene and toluene, methylene chloride, chloroform, or combinations thereof. When the mixture of the color-changing composition and an organic solvent is formed, the mixture is liquid at room temperature. The volatile organic solvent evaporates when the color-changing composition is applied to the substrate.

Binders are used for at least three reasons. First, binders serve to make the color-changing composition more viscous and therefore, more suitable for printing. Second, binders serve to protect the molecules responsible for the color change from environmental moisture experienced as humidity. Finally, binders create stronger adhesion between the composition molecules and the support onto which the color-changing composition will be disposed. Suitable binders include nitrocellulose, cellulose acetate propionate, cellulose acetate butyrate and other non-water soluble binders.

The leuco dyes can be present in the composition from about 0.01 wt. % to about 10 wt. %. Typically the amount of leuco dye can be between about 0.05 or 0.1 wt. % to about 4 or 5 wt. %, or 6 or 7 wt. %; desirably the range is between about 0.5 or 1 wt. % to about 2.5, 3 or 5 wt. %, inclusive. The amount of color developers typically are present from about 1 wt. % to about 10 wt. % or 25 wt. %. The amount of desensitizers typically are present from about 1 wt. % to about 15 wt. % or 30 wt. %. Alternatively, the desensitizers can be present from about 1, 10, or 25 wt. % to about 1, 5, or 15 wt. %, inclusive. The volatile organic solvents can be present from about 20 wt. % to about 90 wt. %; typically between about 25, 30, or 35 wt. % to about 80, 85, or 88 wt. %, inclusive. The binders can be present from about 10, 20, or 30 wt. %.

The wetness indicating inks can be deposited on various material substrates by printing methods (e.g. flexographic and gravure), silk screening, spraying, dipping or any other method for applying an ink composition onto a substrate surface. For example, the ink composition of the present disclosure may be deposited on a material that is used as a component of an absorbent article. The wetness indicating inks may be air-dried and have a colorless or nearly colorless state of appearance (i.e., either no color or very weak background shade).

Once the homogeneous solution is printed and dried on the surface of a substrate, the dried solution can manifest color when in contact with an aqueous medium.

According to certain embodiments, it is desirable to have the ink cover the substrate at least in part, or form indicia on a visually perceivable surface of the substrate. The indicia can be useful when the substrate is part of either an absorbent article or a personal care product that may contact an aqueous solution such as urine. The absorbent article may, for example, be a diaper, feminine hygiene pad, adult incontinence article or a wipe.

The absorbent article may comprise a polymeric film or nonwoven substrate surface having at least a portion of the substrate surface printed with the ink composition of the present disclosure. The substrate can be cellulose-based tissue, paper, a porous film or non-porous film, or a combination of both kinds of films. The porous films may include nonwoven materials, or breathable films, such as polyethylene and polyproplylene films imbedded with calcium carbonate.

Figure 1A:
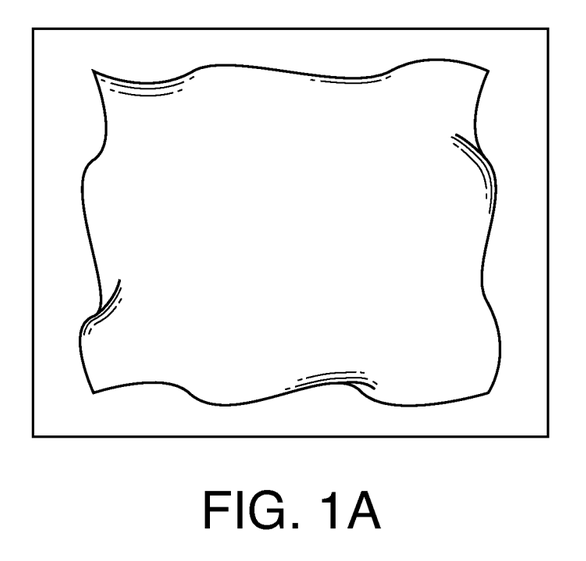
FIG. 1A shows a substrate having an ink composition of the present disclosure deposited thereon and dried, where the ink has a largely colorless appearance.
Figure 1B:
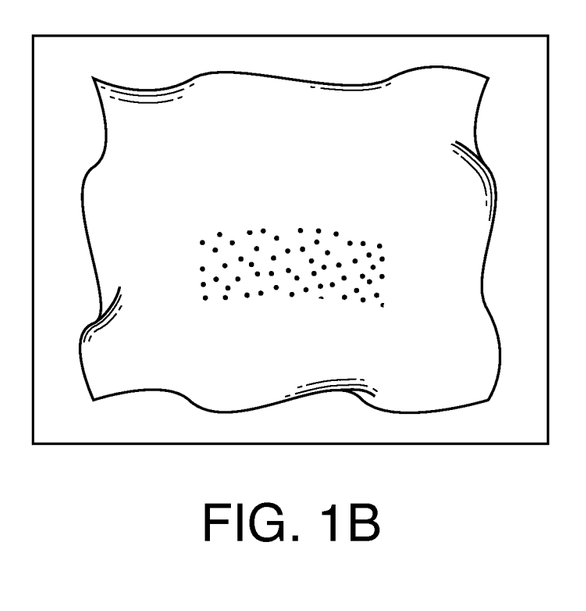
FIG. 1B shows the development of color on the substrate of FIG. 1A after an aqueous solution has reacted with the ink composition.

FIGS. 1A-1B are illustrations that show a substrate surface that has been printed with ink according to the present invention. FIG. 1A shows the substrate at an initial stage with a largely colorless appearance. FIG. 1B shows the same substrate almost immediately after the printed area contacts an aqueous-based fluid.

Typically, after wetting the printed surface at room temperature, depending on the color-changing component concentration in an ink composition and the volume of urine or other liquid insult, color will appear within seconds.

EXAMPLES

The following ink components were blended together to form wetness indicating compositions or inks for the purpose of demonstrating the effectiveness of using a low molecular-weight desensitizer according to the present disclosure.

DYE: CVL Solution: Crystal Violet Lactone CVL and 22.5 mg/ml acetone.
DYE: RED 40 Solution: RED 40, and 31 mg/ml acetone suspension.
DEVELOPER: Zinc Salicylate Solution: Zinc Salicylate and 34.4 mg/ml acetone.
DEVELOPER: Propyl Galate Solution: Propyl Galate and 48.9 mg/ml acetone.
DESENSITIZER: Betaine Solution: Betaine and 160 mg/ml ethanol.

Example #1

100 µl of CVL solution, 20 µl of Zinc Salicylate solution and 50 µl of Propyl Galate solution were mixed together to form a blue solution. When 10 µl of betaine solution was added to 60 µl of the blue solution, the blue solution immediately changed to a colorless state. No binder was added. The colorless solution was applied to a polypropylene film and air dried.

By using a Tack Index Evaluation, the sticky index was rated 1. After blotting the wet area of the film with paper, no leaching of the CVL dye was observed.

Example #2

100 µl of CVL, 30 µl of Zinc Salicylate solution and 70 µl of Propyl Galate solution were mixed together to form a blue solution. When 10 µl of betaine solution was added to 60 µl of the blue solution, the blue solution immediately changed to a colorless state. No binder was added. The colorless solution was applied to polyethylene films containing calcium carbonate and air dried.

By using a Tack Index Evaluation, the sticky index was rated 1. After blotting the wet area of the film with paper, no leaching of the CVL dye was observed.

Example #3

100 µl of RED 40 dye, 30 µl of Zinc Salicylate solution and 70 µl of Propyl Galate solution were mixed together to form a pink solution. 10 µl of betaine solution was added to 60 µl of the pink solution, the pink solution immediately changed to a colorless state. The colorless solution was applied to polyethylene films containing calcium carbonate and allowed to air dry.

By using a Tack Index Evaluation, the sticky index was rated 1. Using a pipette to remove remaining water from a wetted area, no leaching of the RED 40 dye was observed.

Example #3-1

Figure 2:
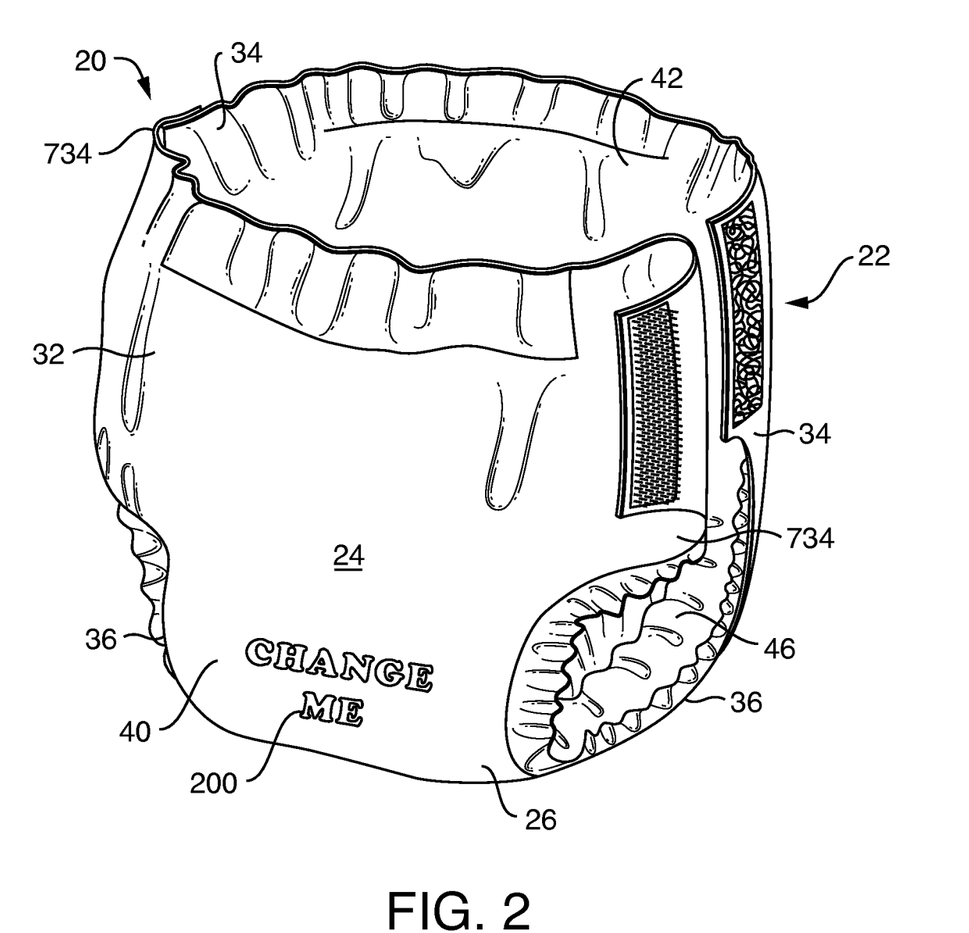
FIG. 2 is a front perspective view of one embodiment of an absorbent article.

Of 4,4'-dihydroxybenzophenone 34.5 mg and cellulose acetate butyrate was dissolved in 200 µl of a 1:1 mixture of n-propylacetate and ethanol. 1.4 mg of Red 40 dye was added to the above pink solution and the resulting solution became red-purple in color. When 100 µl of betaine solution was added to 100 µl of the red-purple solution, it became colorless. The colorless solution was deposited onto a polyethylene film containing calcium carbonate and air dried to form a colorless film. The colorless film was placed on the body-facing surface of the outer cover of a disposable diaper (HUGGIES brand). Referring to FIG. 2, when the diaper was insulted with water, the colorless film became pink and was easily viewed from the garment-facing surface of the outer cover.

Example #3-2

Using the colorless solution of Example 6, the word HoHo! (not shown) was printed on a polyethylene film containing calcium carbonate using a rubber stamp and allowed to air dry. The printed film was then used as a diaper outer cover, and was oriented so that the printed surface coincided with the body-facing surface of the outer cover. The diaper was insulted with water and the pink-colored HoHo! lettering, which quickly appeared at the outer cover, was easily viewed from the garment-facing surface. The visual communication could be any alphanumeric message or indicia, for example, the words "Change Me" as shown in FIG. 2.

Example #3-3

The colorless film of Example #3-2 was put into a glass vial and sealed. The glass vial was placed into a humidity chamber at 40 degrees C., 80% RH. When the vial was kept tightly sealed, the word on the film remained colorless for three hours. When the seal of the vial was compromised, the pink-colored word HoHo! appeared.

Example #4

0.0367 g of Crystal violet lactone, 0.0123 g of zinc salicylate and 0.0624 g of propyl gallate were dissolved in 1 ml of acetone to make a blue-colored crystal violet lactone (CVL) solution. Betaine was dissolved in ethanol at 80 mg/ml. 100 µl of the blue-colored CVL solution was mixed with 100 µl of nitrocellulose solution (a binder) and 160 µl of betaine solution. The blue color immediately changed to a colorless state. The colorless solution was rolled onto a piece of propylene film and allowed to air dry.

By using a Tack Index Evaluation, the tack index was rated 1. After exposing the dried colorless film to water, the contacted area immediately changed to deep blue.

Example #5

0.0367 g of Crystal violet lactone, 0.0123 g of zinc salicylate and 0.0624 g of propyl gallate were dissolved in 1 ml of acetone to make a blue-colored crystal violet lactone (CVL) solution. Betaine was dissolved in ethanol at 80 mg/ml. 100 µl of the blue-colored CVL solution was mixed with 60 µl of hydroxypropyl cellulose ethanol solution (a binder) and 160 µl of betaine solution. The blue color immediately changed to a colorless state. The colorless solution was brushed onto a piece of propylene film and allowed to air dry.

By using a Tack Index Evaluation, the tack index was rated 1. After exposing the dried colorless film to water, the contacted area immediately changed to deep blue.

Example #6

0.0122 g of Crystal violet lactone (CVL), and 0.021 g of 4,4'-dihydroxybenzophenone were dissolved in 333 µl of binder solution (1 ml n-propyl acetate: 1 ml ethanol with 0.2 g of cellulose acetate propionate) to make a blue solution. Betaine was dissolved in ethanol at 80 mg/ml. 100 µl of the blue solution was mixed with 100 µl of betaine solution. The blue color immediately changed to a colorless state. The colorless solution was printed onto a piece of propylene film and allowed to air dry.

By using a Tack Index Evaluation, the tack index was rated 1. After exposing the dried colorless film to water, the contacted area immediately changed to deep blue.

Example #7

Polyethylene glycol (PEG): MW 200 to 35,000. 200 mg Crystal violet lactone and 900 mg of 4,4'-dihydroxybenzophenone were dissolved in 8 ml of nitrocellulose solution (varnish) to make a blue solution.

When 100 µl of polyethylene glycol (MW 200) was mixed with 200 µl of the blue solution, the blue color immediately changed to a colorless state.

Printing the colorless solution with a brush or a roller onto a piece of propylene film and allowing it to air dry resulted in a colorless film.

By using a Tack Index Evaluation, the tack index was rated 5. After exposing a portion of the dried colorless film to an aqueous solution, the wetted area immediately changed to deep blue color. There were similar results for other PEGs having different molecular weights within the 200 to 35,000 range.

Example #8

Polyethylene glycol dimethyl ether (PEG-DE): MW 250 to MW 2,000. 100 mg of Crystal violet lactone and 225 mg of 4,4'-dihydroxybenzophenone were dissolved in 2 ml of nitrocellulose solution (varnish) to make a blue solution.

When 10 µl of PEG-DE (MW 1,000) was mixed with 200 µl of the blue solution, the blue color immediately changed to a colorless state.

Printing the colorless solution with a brush or a roller onto a piece of propylene film and allowing it to air dry resulted in a colorless film. By using a Tack Index Evaluation, the tack index was rated 5. After exposing a portion of the dried colorless film to an aqueous solution, the wetted area immediately changed to deep blue color.

When wetted, similar formulations having MW 250 PEG-DE or MW 500 PEG-DE reacted differently than the MW 1,000 PEG-DE formulation. The MW 250 and MW 500 formulations developed color relatively slowly, and did not develop a deep blue color. Instead, the color was had a lighter value and was less intense.

When wetted, a similar formulation with MW 2,000 PEG-DE having did not develop any color at all, but instead remained colorless.

Example 9

100 mg of crystal violet lactone (leuco dye) and 225 mg 4,4'-dihydroxybenzophenone (developer) were dissolved in 2 ml of nitrocellulose solution (varnish) to make the blue colored crystal violet lactone solution (Solution B). When 10 µl of polyethylene glycol dimethyl ether (MW 1000) (desensitizer) was mixed with 200 µl of Solution B, the blue color immediately changed to an almost colorless state (pale blue).

The colorless solution was printed onto a piece of propylene film with a roller and air dried, resulting in a largely colorless film.

By using a Tack Index Evaluation, the perceived tack index was 5. After exposing the specimen to water or synthetic urine, the specimen immediately changed to a deep blue color.

Example 10

100 mg of crystal violet lactone (leuco dye) and 225 mg of 4,4'-dihydroxybenzophenone (developer) were dissolved in 2 ml of nitrocellulose solution (varnish) to make the blue colored crystal violet lactone solution (Solution B). 10 µl of polyethylene glycol dimethyl ether (MW 2000) (desensitizer) was mixed with 200 µl of Solution B. However, the blue color did not change to a colorless state. Therefore, this formulation is not useful as a color change indicator.

Example 11

Five solutions were formulated according to Table 1. Using the five solutions, specimens were prepared according to the Modified Test Method described herein. Results of the tests are shown in Table 2.

TABLE 1

|  | Solution 1 | Solution 2 | Solution 3 | Solution 4 | Solution 5 |
|---|---|---|---|---|---|
| Desensitizer | Betaine, 50 mg (5%) | Girard's reagent, 100 mg (10%) | PEG (MW 300), 100 μl (10%) | 18-Crown-6-Ether, 80 mg (8%) | PEI (ethylenediamine end-capped) (MW 800), 100 μl (10%) |
| Dye | Crystal Violet Lactone, 5 mg (0.5%) | | | | |
| Developer | 4,4'-Dihydroxybenzophenone, 50 mg (5%) | | | | |
| Binder | Nitrocellulose, 100 mg (10%) | | | | |
| Solvent | Acetone:Ethanol = 1:1 mixture, 1 ml | | | | |

TABLE 2

|  | Solution 1 Betaine (gf) | Solution 2 Girard's reagent (gf) | Solution 3 PEG (gf) | Solution 4 18-Crown-6-Ether (gf) | Solution 5 PEI (gf) |
|---|---|---|---|---|---|
| Specimen 1 | 1.39 | 0 | 7.32 | 5.52 | 9.02 |
| Specimen 2 | 0 | 0 | 4.67 | 8.01 | 14.99 |
| Specimen 3 | 0.98 | 0 | 9.32 | 2.50 | 13.00 |
| Specimen 4 | 0 | 0 | 5.24 | 13.53 | 13.59 |
| Specimen 5 | 0 | 0 | — | — | 10.17 |
| Average | 1.19 | 0 | 6.64 | 7.39 | 12.15 |
| Tack Rating | Non-tacky | Non-tacky | Tacky | Tacky | Tacky |
| Tack Index | 1 | 1 | 5 | 7 | 7 |

It is noted that the Tack Rating and the Tack Index each indicate that PEG, 18-Crown-6-Ether, and PEI are not suitable desensitizers for the ink formula. The betaine and Girard formulations exhibit the lowest Tack Index and Tack Rating, and are therefore suitable desensitizers for the wetness indicator composition of the present disclosure.

Test Methods

Tack Index Evaluation: Qualitative tackiness is determined using the following non-standard method. Apply the colorless ink solution with a brush or a roller onto a piece of propylene film and let it air dry under ambient conditions. Use an index finger to touch the coated dry film surface. On a scale of 1 to 10, rate the stickiness of the coated films, wherein 1 is non-tacky and 10 is very tacky.

Modified ASTM Standard D3330/D3330M-04: Standard Test Method for Peel Adhesion of Pressure-Sensitive Tape: Quantitative tackiness is determined using a modification of a standard test method. Basically, a film having the formulation of the present disclosure printed thereon is substituted for the pressure-sensitive tape.

Test conditions are held at 25 degrees C. and 50% relative humidity.

Prepare samples by cutting strips of polypropylene film having a calcium carbonate filler and of sufficient stiffness, each strip having the dimensions of 24 mm in width and 300 mm in length.

Attach a paper strip to one end of each sample, the paper strip having a dimension of about 24 mm in width and 40 mm in length. The paper strip functions as a non-tacky grip.

Coat 300 μl of an ink formula shown in Table 1 onto the one side of a film sample using a roller. Prepare 5 specimens for each ink formula.

Cover the coated area of each specimen with an uncoated film of the same type of dimensions and paper strip as the sample so that their respective axes are aligned in the same direction. The paper strips overlap.

Apply pressure to each specimen for five minutes with a 2 kg block having a length of 22 cm, a width of 2.5 cm and a height of 4.5 cm. Place the 22 cm by 2.5 cm block face against the specimen to apply a pressure of 36.4 g/cm$^2$. Remove the block and allow the specimen to dry under ambient conditions for one hour.

The 180 degree peel test is performed using a 10N load cell in tension mode. A constant-rate-of-extension (CRE) tension tester (e.g. INSTRON tensile tester) is used. The tester has two clamps with centers in the same plane, parallel with the direction of the motion on the stressing clamp, and aligned so that they will hold the specimen wholly in the same plane. The tester has a means of moving the stressing clamp at a uniform rate of 0.2 mm/s [0.5 in/min] and a device for recording load. The instrument is calibrated to an accuracy of 0.5% of full scale and the scale range used for any test shall be such that the mean test level falls within 20 to 80% of full scale. Test variations are likely due to non-uniform coating thickness.

Clamp the papered end of the specimen into the movable jaw of the testing machine and the opposite end of the specimen into the other jaw. Operate the movable jaw at 5.08 cm/minute. After the movable jaw is started in motion, disregard the values obtained while the first 25 mm [1 in] of the specimen is mechanically peeled. Use the average force obtained during peeling of the next 50 mm as the adhesion value.

The peel rate is 5.08 cm/minute. The test sensitivity is 5 percent.

Exemplary Absorbent Article

The composition of the present disclosure is useful for application to disposable absorbent articles such as pants, diapers and pads. An absorbent article of the present invention generally can have an absorbent core, and can optionally include a topsheet and/or a backsheet, where the absorbent core can be disposed between the topsheet and the backsheet. To gain a better understanding of the present invention, attention is directed to FIGS. 2 and 3 for exemplary purposes showing a training pant and a signal composite of the present invention.

Various materials and methods for constructing training pants are disclosed in U.S. Pat. No. 6,761,711 to Fletcher et al.; U.S. Pat. No. 4,940,464 to Van Gompel et al.; U.S. Pat. No. 5,766,389 to Brandon et al., and U.S. Pat. No. 6,645,190 to Olson et al., each of which is incorporated herein by reference in a manner that is consistent herewith.

Figure 3:
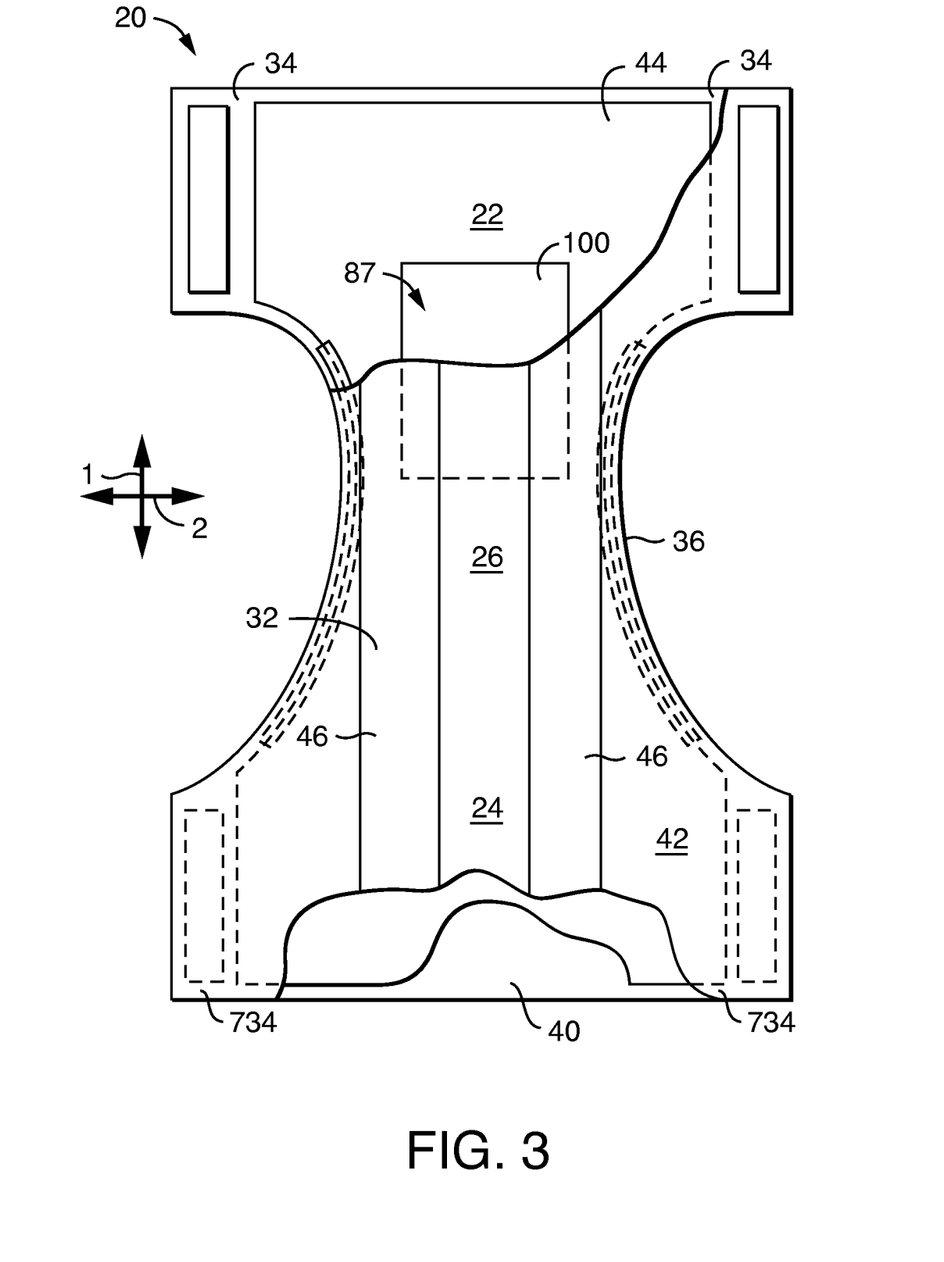
FIG. 3 is a plan view of the absorbent article of FIG. 2, in an unfastened, unfolded, and laid out flat configuration.

FIG. 2 illustrates a training pant 20 in a partially fastened condition, and FIG. 3 illustrates a training pant 20 in an opened and unfolded state. The training pant 20 defines a longitudinal direction 1 that extends from the front of the training pant when worn to the back of the training pant. Perpendicular to the longitudinal direction 1 is a lateral direction 2.

The training pant 20 defines a front region 22, a back region 24, and a crotch region 26 extending longitudinally between and interconnecting the front and back regions. The pant 20 also defines an inner surface (i.e., body-facing surface) adapted in use (e.g., positioned relative to the other components of the pant) to be disposed toward the wearer, and an outer surface (i.e., garment-facing surface) opposite the inner surface. The training pant 20 has a pair of laterally opposite side edges and a pair of longitudinally opposite waist edges.

The illustrated pant 20 may include a chassis 32, a pair of laterally opposite front side panels 34 extending laterally outward at the front region 22 and a pair of laterally opposite back side panels 734 extending laterally outward at the back region 24. The pant 20 further includes a sensor 100 that is placed, for example, between the absorbent core 44 and the topsheet 42 so that the sensor surface 87 is revealed from the inside of the pant 20. In an alternative (not shown), the sensor 100 is located between the backsheet 40 and the absorbent core 44 so that it may be viewed through the backsheet. Sensor 100 may be located anywhere on the absorbent article where wetness sensing is desired.

The chassis 32 includes a backsheet 40 and a topsheet 42 that may be joined to the backsheet 40 in a superimposed relation therewith by adhesives, ultrasonic bonds, thermal bonds or other conventional techniques. The chassis 32 may further include an absorbent core 44, such as shown in FIG. 3, disposed between the backsheet 40 and the topsheet 42 for absorbing fluid body exudates exuded by the wearer, and may further include a pair of containment flaps 46 secured to the topsheet 42 or the absorbent core 44 for inhibiting the lateral flow of body exudates.

The backsheet 40 may be constructed of a nonwoven material. The backsheet 40, may be a single layer of a fluid impermeable material, or alternatively may be a multi-layered laminate structure in which at least one of the layers is fluid impermeable.

Examples of suitable backsheet 40 materials are spunbond-meltblown fabrics, spunbond-meltblown-spunbond fabrics, spunbond fabrics, or laminates of such fabrics with films, or other nonwoven webs; elastomeric materials that may include cast or blown films, meltblown fabrics or spunbond fabrics composed of polyethylene, polypropylene, or polyolefin elastomers, as well as combinations thereof. The backsheet 40 may include materials that have elastomeric properties through a mechanical process, printing process, heating process or chemical treatment. For example, such materials may be apertured, creped, neck-stretched, heat activated, embossed, and micro-strained, and may be in the form of films, webs, and laminates.

One example of a suitable material for a biaxially stretchable backsheet 40 is a breathable elastic film/nonwoven laminate, such as described in U.S. Pat. No. 5,883,028, to Morman et al., incorporated herein by reference in a manner that is consistent herewith. Examples of materials having two-way stretchability and retractability are disclosed in U.S. Pat. No. 5,116,662 to Morman and U.S. Pat. No. 5,114,781 to Morman, each of which is incorporated herein by reference in a manner that is consistent herewith.

The topsheet 42 is suitably compliant, soft-feeling and non-irritating to the wearer's skin. The topsheet 42 is also sufficiently liquid permeable to permit liquid body exudates to readily penetrate through its thickness to the absorbent core 44. A suitable topsheet 42 may be manufactured from a wide selection of web materials, such as porous foams, reticulated foams, apertured plastic films, woven and non-woven webs, or a combination of any such materials. For example, the topsheet 42 may include a meltblown web, a spunbonded web, or a bonded-carded-web composed of natural fibers, synthetic fibers or combinations thereof. The topsheet 42 may be composed of a substantially hydrophobic material, and the hydrophobic material may optionally be treated with a surfactant or otherwise processed to impart a desired level of wettability and hydrophilicity.

The topsheet 42 may also be extensible and/or elastomerically extensible. Suitable elastomeric materials for construction of the topsheet 42 can include elastic strands, LYCRA elastics, cast or blown elastic films, nonwoven elastic webs, meltblown or spunbond elastomeric fibrous webs, as well as combinations thereof. Examples of suitable elastomeric materials include KRATON elastomers, HYTREL elastomers, ESTANE elastomeric polyurethanes (available from Noveon, a business having offices located in Cleveland, Ohio U.S.A.), or PEBAX elastomers. The topsheet 42 can also be made from biaxially stretchable materials as described in U.S. Pat. No. 6,969,378 to Vukos et al. which is incorporated herein by reference in a manner that is consistent herewith.

The article 20 can optionally further include a surge management layer which may be located adjacent the absorbent core 44 and attached to various components in the article 20 such as the absorbent core 44 or the topsheet 42 by methods known in the art, such as by using an adhesive. Examples of suitable surge management layers are described in U.S. Pat. No. 5,486,166 to Bishop et al.; U.S. Pat. No. 5,490,846 to Ellis et al.; and U.S. Pat. No. 5,820,973 to Dodge et al., each of which is incorporated herein by reference in a manner that is consistent herewith.

The article 20 can further comprise an absorbent core 44. The absorbent core 44 may have any of a number of shapes. The absorbent core 44 can be attached in an absorbent article, such as to the backsheet 40 and/or the topsheet 42 for example, by bonding means known in the art, such as ultrasonic, pressure, adhesive, aperturing, heat, sewing thread or strand, autogenous or self-adhering, hook-and-loop, or any combination thereof.

The absorbent core 44 can be formed using methods known in the art. While not being limited to the specific method of manufacture, the absorbent core can utilize forming drum systems, for example, see U.S. Pat. No. 4,666,647 to Enloe et al., U.S. Pat. No. 4,761,258 to Enloe, U.S. Pat. No. 6,630,088 to Venturino et al., and U.S. Pat. No. 6,330,735 to Hahn et al., each of which is incorporated herein by reference in a manner that is consistent herewith. Examples of techniques which can introduce a selected quantity of optional superabsorbent particles into a forming chamber are described in U.S. Pat. No. 4,927,582 to Bryson and U.S. Pat. No. 6,416,697 to Venturino et al., each of which is incorporated herein by reference in a manner that is consistent herewith.

In some desirable aspects, the absorbent core includes cellulose fiber and/or synthetic fiber, such as meltblown fiber, for example. Thus, in some aspects, a meltblown process can be utilized, such as to form the absorbent core in a coform line. In some aspects, the absorbent core 44 can have a significant amount of stretchability.

The absorbent core 44 can additionally or alternatively include absorbent and/or superabsorbent material. Accordingly, the absorbent core 44 can comprise a quantity of superabsorbent material and optionally fluff contained within a matrix of fibers. It should be understood that the absorbent core 44 is not restricted to use with superabsorbent material and optionally fluff. In some aspects, the absorbent core 44 may additionally include materials such as surfactants, ion exchange resin particles, moisturizers, emollients, perfumes, fluid modifiers, odor control additives, and the like, and combinations thereof. In addition, the absorbent core 44 can include foam.

The present invention has been described both generally and in detail by way of examples and the figures. Persons skilled in the art, however, can appreciate that the invention is not limited necessarily to the embodiments specifically disclosed, but that substitutions, modifications, and variations may be made to the present invention and its uses without departing from the spirit and scope of the invention. Therefore, changes should be construed as included herein unless the modifications otherwise depart from the scope of the present invention as defined in the following claims.

The invention claimed is:

1. A color-developing composition comprising:
a color-appearing leuco dye;
a color-developer; and
a desensitizer;
wherein the desensitizer is a zwitterionic small molecule having a molecular weight of 100 to 800.

2. The color-developing composition of claim 1 wherein the desensitizer comprises betaine.

3. The color-developing composition of claim 1 wherein the desensitizer is selected from the group consisting of poly sugar betaine C, Betaine ester-menthol and Betaine hydrochloride.

4. The color-developing composition of claim 1 wherein the desensitizer is soluble in a volatile organic solvent and water.

5. The color-developing composition of claim 4 wherein the volatile organic solvent comprises ethanol.

6. The color-developing composition of claim 1 wherein the leuco dye and color developer are water insoluble.

7. The color-developing composition of claim 1 wherein the desensitizer comprises Girard's reagent.

8. The color-developing composition of claim 1 wherein the molecular weight is 100 to 500.

9. The color-developing composition of claim 1 wherein the molecular weight is 200 to 400.

10. The color-developing composition of claim 1 wherein the zwitterionic molecules comprises 2-(methacryloyloxy) ethyl 3-sulfopropyl)ammonium hydroxide.

11. The color-developing composition of claim 1 further comprising a binder.

12. The color-developing composition of claim 11 wherein the binder is water soluble.

13. The color-developing composition of claim 1 wherein the color-developer comprises bisphenol A, zinc chloride, zinc salicylate, and/or phenol resins.

14. The color-developing composition of claim 1 wherein the leuco dye comprises phthalide leuco dye, triarylmethane leuco dye, and/or fluoran leuco dye.

15. A color changing material comprising:
a substrate having an ink deposited thereon;
wherein the ink comprises a color-appearing leuco dye; a color-developer; and
a desensitizer; and
wherein the desensitizer is selected from the group consisting of betaine and/or Girard's reagent.

16. The color changing material of claim 15 wherein the substrate is a porous material.

17. The color changing material of claim 15 comprises a synthetic polymer.

18. An absorbent article with a color-changing feature, the absorbent article comprising:
a topsheet;
a backsheet having a garment-facing surface and an opposite body-facing surface;
an absorbent core disposed between the topsheet and the back sheet; and
a color-changing composition comprising a leuco-dye and a developer, the color-changing composition deposited onto the body-facing surface of the backsheet; the color-changing composition further comprising a zwitterionic small molecule desensitizer having a molecular weight between 100 and 500.

19. The absorbent article of claim 18 wherein the color-changing composition comprises betaine.

20. The absorbent article of claim 18 wherein the color-changing composition forms indicia.

* * * * *